United States Patent
Birkholz et al.

(10) Patent No.: US 9,638,617 B2
(45) Date of Patent: May 2, 2017

(54) MEMS-MICROVISCOMETER

(71) Applicant: IHP GmbH, Frankfurt (DE)

(72) Inventors: Mario Birkholz, Frankfurt (DE);
Jurgen Drews, Frankfurt (DE);
Karl-Ernst Ehwald, Frankfurt (DE);
Dieter Genschow, Rudersdorf OT Herzfelde (DE); Ulrich Haak, Frankfurt (DE); Philip Kulse, Berlin (DE);
Egbert Matthus, Frankfurt (DE);
Katrin Schulz, Frankfurt (DE);
Wolfgang Winkler, Frankfurt (DE);
Dirk Wolansky, Frankfurt (DE);
Marlen Frohlich, Magdeburg (DE)

(73) Assignee: IHP GMBH—INNOVATIONS FOR HIGH PERFORMANCE MICROELECTRONICS/LEIBNIZ-INSTITUT FUR INNOVATIVE MIKROELEKTRONIK, Frankfurt (DE)

( * ) Notice: Subject to any disclaimer, the term of this patent is extended or adjusted under 35 U.S.C. 154(b) by 873 days.

(21) Appl. No.: 13/921,515

(22) Filed: Jun. 19, 2013

(65) Prior Publication Data
US 2014/0000344 A1  Jan. 2, 2014

(30) Foreign Application Priority Data

Jun. 21, 2012 (DE) .................. 10 2012 210 470

(51) Int. Cl.
*G01N 11/00* (2006.01)
*G01N 11/16* (2006.01)

(52) U.S. Cl.
CPC ............. *G01N 11/00* (2013.01); *G01N 11/16* (2013.01)

(58) Field of Classification Search
CPC ........ G01N 11/16; G01N 11/00; G01N 11/02; G01N 11/08

(Continued)

(56) References Cited

U.S. PATENT DOCUMENTS

| 3,137,161 A * | 6/1964 | Lewis ................. G01N 11/04 73/54.04 |
| 5,384,676 A * | 1/1995 | Yokoyama ............ G11B 5/588 360/77.13 |

(Continued)

FOREIGN PATENT DOCUMENTS

| DE | 10027684 A1 | 6/2001 |
| DE | 10010539 A1 | 9/2001 |

(Continued)

Primary Examiner — John Fitzgerald
Assistant Examiner — Truong Phan
(74) Attorney, Agent, or Firm — Ware, Fressola, Maguire & Barber LLP

(57) ABSTRACT

Micro-electromechanical device for measuring the viscosity of a fluid, comprises a measuring chamber with a micromechanical actuator, arranged as a cantilever above a metallically conductive counter electrode, elastically deformable towards the counter electrode, surrounded by the fluid to be measured and made of a metallically conductive material, a two-terminal RF voltage source that can be switched off, having a first output terminal connected to the actuator, and a second output terminal connected to the counter electrode, and which is designed to output an RF voltage signal that is suitable for deflecting the actuator out of its rest position, and a measuring device to detect a change in the frequency, amplitude or phase of the RF signal in order to determine a measurement value for the viscosity-dependent speed at which the actuator is deformed.

16 Claims, 9 Drawing Sheets

(58) Field of Classification Search
USPC .......... 73/54.01, 54.24, 54.25, 54.26, 54.27, 73/54.18, 24.01, 54.23, 54.31
See application file for complete search history.

(56) References Cited

U.S. PATENT DOCUMENTS

| | | | | |
|---|---|---|---|---|
| 5,394,739 A | * | 3/1995 | Garvey, III | ............ G01N 11/14 73/54.15 |
| 5,955,659 A | | 9/1999 | Gupta et al. | |
| 6,210,326 B1 | * | 4/2001 | Ehwald | .............. A61B 5/14532 128/903 |
| 6,260,408 B1 | * | 7/2001 | Vig | ........................ G01N 11/16 73/54.24 |
| 6,651,513 B2 | * | 11/2003 | Wenger | ................. G01F 1/8409 73/54.24 |
| 7,313,945 B2 | | 1/2008 | Giri et al. | |
| 2001/0045122 A1 | | 11/2001 | Ehwald et al. | |
| 2003/0054560 A1 | | 3/2003 | Ehwald et al. | |
| 2006/0283252 A1 | * | 12/2006 | Liu | ..................... G01N 29/022 73/649 |
| 2008/0191710 A1 | * | 8/2008 | Forstner | ................ G01R 29/26 324/614 |
| 2010/0207216 A1 | | 8/2010 | Drews et al. | |
| 2010/0219842 A1 | * | 9/2010 | Gianetti | ................... G01D 5/24 324/662 |

FOREIGN PATENT DOCUMENTS

| | | |
|---|---|---|
| DE | 10 2007 031 128 A1 | 1/2009 |
| DE | 10 2008 016 121 B4 | 3/2010 |
| WO | 2010/123521 A1 | 10/2010 |

* cited by examiner

MEMS-MICROVISCOMETER

CROSS REFERENCE TO RELATED APPLICATIONS

This application claims priority under 35 USC §119 to German Patent Application No. 10 2012 210 470.4 filed on Jun. 21, 2012, which application is hereby incorporated by reference in its entirety.

TECHNICAL FIELD

The invention relates to a MEMS device and a method for measuring the viscosity of extremely small fluid volumes using a micro-viscometer.

BACKGROUND OF THE INVENTION

Micro-viscometers of this type are used, inter alia, in affinity viscometry for determining the glucose content of an analyte, for example of blood. For this purpose, a separating membrane that allows a selective exchange of molecules is arranged between analyte and a measuring fluid, whereby the viscosity of the measuring fluid is directly related to the glucose content of the analyte.

The operating principle of the measuring fluid is based, for example, on the exchange of dextran molecules occupying the sugar-binding sites of a lectin molecule with glucose molecules that diffuse through the separating membrane. Other versions use a polymer solution containing boric acid functional groups as the measuring fluid, as described in WO 2010/0123521.

Micro-viscometers that are particularly suitable for use in affinity viscometry are known in the widest range of embodiments. Basically these embodiments can measure the viscosity by measuring the flow resistance of a moved measuring fluid in a capillary tube (e.g. DE 100 10 539 A1) or by a measuring body moved in the measuring fluid. For miniaturization, micro-electromechanical actuators are used, for example in the form of flexible tabs (cantilevers), which are moved in the measuring fluid and the dynamic response of these cantilevers is measured for a defined drive force. Measuring devices of this type based on a micro-viscometer therefore necessarily contain a drive and a system for measuring the cantilever deflection. For a known geometry and assuming a laminar fluid flow, the viscosity can be determined from the curve of the speed at which such an actuator moves through the measuring fluid for a defined drive force.

U.S. Pat. No. 5,955,659 describes an electrostatically driven cantilever for determining fluid properties. FIG. 1 shows a schematic diagram of this micro-viscometer according to the prior art. Under an electrode 106 of an actuator in the form of an elastically deformable cantilever 105 is located a counter electrode 104 in the form of a ground electrode on a silicon substrate 101 that has an electrically insulating coating 103. Switching on a voltage $V_{in}$ between electrode 106 and counter electrode 104 produces a force of attraction between the electrode 106 and the counter electrode 104 that deforms the cantilever 105. The cantilever is regarded here as a spring/mass system, the movement of which is damped by the viscosity of the fluid to be measured. A simple embodiment of a measuring device comprises a contact which is closed as a result of a predetermined deflection of the cantilever. The time from switching on a drive voltage between cantilever and the ground electrode in the measuring chamber until the contact closes is hence used as a measure for the viscosity. If the drive voltage is then switched off, the elastic cantilever returns to its initial position, and the measurement process can be started again. In a conductive fluid, e.g. in an isotonic saline solution, this form of electrostatic drive cannot be used because the electrodes become polarized within fractions of microseconds, which reduces or eliminates the E-field in the fluid that is required for the drive, or additionally at higher voltages, electrolysis starts, releasing hydrogen. Documents DE 100 27 684 and U.S. Pat. No. 5,955,659 do not discuss these problems.

DE 100 27 684 A1 describes, according to one embodiment of the actuator, an electrical conductor to which a radio-frequency (RF) alternating current is applied and which interacts with another conductor, wherein at least one of these conductors is elastically deformable. A measuring device, which is not described in greater detail, performs a capacitance measurement or an impedance measurement between the movable conductor and a fixed conductor. It recommends choosing the excitation frequency and the frequency used for the impedance measurement to be so high that the force acting on the actuator and the impedance measurement are largely independent of the electrical conductivity of the measuring fluid.

In fact it is advantageous to use for driving the cantilever or a differently designed, elastically movable actuator, an alternating voltage having a frequency that is chosen to be so high that the effects of ion movement and electrode polarization in the measuring fluid on the force moving the actuator are small. The conductance and the frequency dependency of the permittivity of the measuring fluid must be taken into account both for the drive and for the measuring system. Using a DC voltage or a low-frequency voltage is not only unsuitable for the actuator drive in a conductive fluid but also, owing to an ion current and polarization effects on the electrodes, will result in an incorrect capacitive distance measurement, for example.

SUMMARY OF THE INVENTION

According to the invention, a device, referred to below as a MEMS device, is proposed for measuring the viscosity of a fluid, i.e. of a liquid or gas, which device comprises:
- a measuring chamber comprising a micromechanical actuator, which is arranged in the manner of a cantilever above a metallically conductive counter electrode and is elastically deformable towards the counter electrode, and which during operation of the device must be surrounded by the fluid to be measured and is made of a metallically conductive material,
- a two-terminal RF voltage source that can be switched off, the first output terminal of which is connected or can be connected to the actuator, and the second output terminal of which is connected or can be connected to the counter electrode, and which is designed to output an RF voltage signal having an RMS voltage that is suitable for deflecting the actuator out of its rest position, preferably so far that a laminar flow can develop temporarily in the fluid to be measured.
- a measuring device, which is designed to detect a change in the frequency, the amplitude or the phase of the RF signal generated by the RF voltage source in order to determine therefrom a measurement value for the viscosity-dependent speed at which the actuator is deformed.

The MEMS device according to the invention has the advantage over the known prior art of being capable of extreme miniaturization and being suitable for measuring the viscosity in extremely small volumes of the fluid to be measured. In addition, it is particularly suitable for measuring high viscosities in strong electrolytes.

In the MEMS device according to the invention, the RF voltage source used to generate the force to move the actuator towards the counter electrode through the viscous fluid, is the same RF voltage source which provides the measurement signal according to an impedance change of the actuator/counter-electrode system in the form of a frequency change, amplitude change or phase shift of the RF voltage moving the actuator, which signal is detected by the measuring device. Thus there is no need for a separate device, such as e.g. a piezoelectric crystal having a suitable high-voltage source, to drive the actuator, which facilitates a small design, and, in preferred embodiments, in particular facilitates monolithic integration of the actuator system with the electronic circuitry of the RF voltage source and the measuring device.

In medical applications of the MEMS device according to the invention, such as for example in blood-sugar monitoring, the combined advantages of small design and high long-term stability of the biochemical measuring principle mean that the MEMS device can even be implanted permanently. This enables, for instance, continuous monitoring of the blood sugar level and hence individualized adjustment of drug delivery that is always exactly right for the patient concerned.

Exemplary embodiments of the MEMS device according to the invention are described below.

In one embodiment of the MEMS device according to the invention, during operation a variable impedance formed by actuator, measuring fluid and counter electrode is integrated as a frequency-controlling element in an RF oscillator. After switching on the oscillator during operation of the MEMS device, the RF voltage applied between actuator and counter electrode produces an actuator movement, which causes a change in the impedance between actuator and counter electrode and hence changes the frequency of the RF oscillator, which is detected by the measuring device of the MEMS device according to the invention. This frequency change is used to determine a viscosity-dependent speed of the actuator movement.

A preferred exemplary embodiment of the invention is based on the knowledge that using a voltage to drive the actuator can cause a current through the measuring fluid that has a non-negligible effect on the overall measuring arrangement. It is therefore advantageous to use for driving the actuator an alternating voltage having a frequency that is so high that an ion movement in the measuring fluid caused by the alternating voltage only has a small effect on the electrical force moving the actuator and on the impedance of the actuator/counter-electrode system. An RF voltage source having a frequency between 1 GHz and 5 GHz for instance is therefore advantageously used in a physiological (isotonic) saline solution or in salt water.

In this frequency range, in an isotonic saline solution at 40° C., the capacitive impedance $1/\omega C_F (\omega,x)$ between the actuator and counter electrode is less than, preferably half the size of, the ohmic resistance $Ro(x)$ given by the electrical conductivity of the fluid to be measured. Here $\omega$ denotes the angular frequency and x is a measure of the deflection of the actuator. Such a specification for the frequency of the RF voltage source can be guaranteed in the design stage by dimensioning the relevant circuit parameters according to the particular application. This is because a typical range of values of the electrical conductivity of the fluid to be measured is usually known in advance or can be determined from simple tests. In addition to this, a certain adjustability of the frequency during operation can be provided, for example by means of a controllable capacitance. This is discussed in greater detail in exemplary embodiments described later.

In a preferred exemplary embodiment, the RF voltage source is designed to generate an RF voltage between actuator and counter electrode that has an RMS value such that after switching on the RF voltage, the electrical force of attraction between upper actuator and the counter electrode results in a sufficiently large, reversible elastic deflection of the actuator towards the counter electrode in order to produce temporarily a laminar flow field in the immediate vicinity of the actuator. In this case, the speed of the actuator movement at every instant is inversely proportional to the viscosity, provided external acceleration forces and gravitational forces have a negligible effect on the actuator movement and provided this movement is damped by the viscosity of the medium to such an extent that natural resonances do not occur (overdamped condition). If the orientation of the actuator in the gravitational field is variable (the case for portable devices), according to the above provisos it must additionally be ensured that the intrinsic weight of the actuator is negligible compared with the electrical force of attraction between actuator and counter electrode, because otherwise the measurement result depends on the orientation of the MEMS device in the gravitational field.

In an embodiment of the MEMS device, the measuring device for determining the viscosity-dependent timespan is designed to switch on the RF voltage source, to switch off the RF voltage source when the predefined deformation of the actuator is reached (which is detected, for instance, in the form of a predefined magnitude of a frequency change, amplitude change or phase shift), and to determine the timespan between switching on and switching off the RF voltage source and to output a measurement signal that is dependent on the timespan as a measure of the viscosity of the fluid to be measured.

"Switching off" shall be understood to mean any form of interrupting the RF voltage across the actuator. In this context, switching off is, for example, a switching process in which a supply of power from the RF voltage source is reversibly interrupted using a switch. Alternatively, an RF voltage supply to the actuator can also be reversibly interrupted without switching off the RF voltage source.

If a frequency change of the RF voltage source is used as a measurement signal for monitoring the actuator movement, then this voltage source can be designed as a ring oscillator comprising an odd number of CMOS inverter stages, wherein an output from one of the CMOS inverter stages can be connected or is connected to the actuator either directly or via a coupling capacitor, and an RF ground terminal of the ring oscillator can be connected or is connected to the counter electrode.

In a preferred embodiment, the actuator is here connected directly or via a coupling capacitor to the connecting line between the output of one CMOS inverter stage and the input of the subsequent inverter stage of the ring oscillator.

In a further embodiment, the actuator/counter-electrode system is integrated in the ring oscillator circuit as a two-port network. For this purpose, the actuator has two spaced-apart electrical terminals, wherein the first terminal is connected to the output of a first inverter stage, the second electrical terminal of the actuator is connected to the input of a second ring-oscillator inverter stage following the first stage.

In both cases, the impedance change of the actuator/counter-electrode system caused by the actuator movement affects the speed of the signal transfer between two successive inverter stages and hence affects the ring oscillator frequency.

The oscillator can also be implemented as an LC oscillator, however, wherein the impedance formed between actuator and counter electrode is integrated in the LC resonant circuit.

In order to implement a particularly accurate measuring device, the MEMS device in preferred exemplary embodiments additionally comprises a reference oscillator, which is designed to generate an RF reference signal having a reference frequency that is relatively constant over time and does not depend on the actuator movement.

The reference frequency can be used in various ways in different variants of the measuring device. In a first variant, the measuring device is designed to switch on the reference oscillator at the same time as the measurement oscillator, and to generate a switch-off signal when the difference between the frequency of the RF reference signal output by the reference oscillator and the frequency of the measurement oscillator reaches a predefined value. A second variant, however, in which the measuring device is designed to compare the frequency of the measurement oscillator with the reference frequency, and to generate a switch-off signal at that instant at which the frequency of the measurement oscillator has reached the reference frequency, has simpler circuitry and is therefore preferred. In this second variant, the reference frequency is thus used as a "target frequency", the attainment of which by the measurement oscillator terminates the measurement process.

A lock detector, frequency detector or a phase-frequency detector can be provided as part of the measuring device to compare the frequencies of reference oscillator and measurement oscillator. Using a lock detector or frequency detector means less circuit complexity compared with a phase-frequency detector without substantial loss of accuracy and is therefore preferred. The lock detector, frequency detector or the phase-frequency detector is designed to compare the frequency of the RF voltage signal output by the measurement oscillator with the reference frequency, and, at the instant at which the frequency of the measurement oscillator has reached the reference frequency, to generate the switch-off signal, which causes the measurement oscillator and the reference oscillator to switch off.

The reference oscillator is preferably connected to a reference structure that is similar to the actuator system and which during operation of the device, like the actuator system, must be surrounded by the fluid to be measured. In this embodiment, the measurement oscillator and the reference oscillator have substantially or almost exactly the same dimensions, wherein the reference structure has a reference impedance that is identical or almost identical to the impedance value that exists between the actuator and the counter electrode of the actuator system at the instant in time of switching off. The reference oscillator comprises e.g. a reference chamber, which in order to form the reference capacitance has a micromechanical, non-deformable reference actuator that has the same dimensions as the actuator and is arranged in the manner of a cantilever above a metallically conductive reference counter electrode made with the same dimensions as the counter electrode, which reference actuator must be surrounded by the fluid to be measured during operation of the device, and is made of the same metallically conductive material. It is important that under operating conditions of the MEMS device, the reference actuator, unlike the actuator of the measurement oscillator, cannot be deformed, i.e. in particular does not move when an RF signal is applied.

To enable fine adjustment of an initial frequency difference between the measurement oscillator and the reference oscillator that exists immediately after switching on the voltage supply, in an advantageous embodiment the reference oscillator or the measurement oscillator additionally contains as a frequency-setting component a capacitance that can be controlled externally by a control voltage, for example in the form of a varicap diode or a MOS varactor. The additional controllable capacitance is connected in parallel with the capacitance formed by actuator and counter electrode. The voltage-controlled capacitance is preferably dimensioned so that based on an initial frequency difference that can be set by said capacitance, at the time of switching off the supply voltage at the limit of travel of the actuator movement, no mechanical contact is made between counter electrode and actuator.

In principle, any known cantilever structures can be used as the actuator. In a preferred embodiment, however, the actuator is fixed to an edge of the measuring chamber at at least two opposite points of the measuring chamber and comprises an elastic element. Such an elastic element increases the elastic flexibility of the actuator. Any reference actuator there may be is also in this exemplary embodiment fixed to the edge of the reference chamber at at least two opposite points of the reference chamber, but does not contain an elastic element in order to prevent the reference actuator being deformable, which as explained is unwanted.

The actuator is preferably made of conductive TiN for the purpose of measuring the viscosity in a medium containing constituents of an animal bodily fluid and having high salinity.

The geometry of the actuator can be tailored, i.e. the shape and dimensions can be correlated for operation of the MEMS device such that, for the given frequency of the RF voltage source (ignoring small dielectric losses in the fluid to be measured), a real part of the complex RF impedance between actuator and counter electrode, which real part is attributable to a sheet resistance of the actuator, is comparable to or greater than the magnitude of the capacitive reactance (imaginary part) $1/\omega C$ when the RF voltage source is switched on.

In a specific embodiment, the RF voltage source is designed as a ring oscillator and coupled to the actuator impedance such that, because of the high real part of the impedance, the frequency of the RF voltage signal paradoxically rises as the capacitive reactance $1/\omega C$ drops during movement of the actuator towards the ground plate. A design having such dimensions can be useful, for example, if for a frequency of several GHz, very thin and relatively long TiN strips having a relatively high sheet resistance (e.g. >20 Ohms) are arranged in the actuator at a very short separation from the counter electrode (e.g. several μm) in order to improve the elasticity of the actuator and to reduce the RMS voltage required for moving the actuator. In this case, the phase shift between voltage and current measured across the actuator/counter-electrode system connected as a two-terminal device may reduce as the capacitance, which is related to surface area, increases, because then for a very high frequency, the ohmic resistance of the actuator material increasingly determines the impedance between actuator and counter electrode. The resultant reduced signal delay between two inverter stages of a ring oscillator results in the apparently paradoxical frequency rise mentioned above. This frequency rise can then be used, just like the case in which a frequency drop is observed for a low-resistance actuator material, to switch off the operating voltage when a defined frequency, e.g. a suitably set reference frequency, is reached, and to determine the corresponding viscosity-dependent switch-off time.

The MEMS device according to the invention can advantageously be used in medical or biological applications, for instance as a sensor for determining the blood sugar content based on the principle of affinity viscosity. A viscosity sensor according to the present invention can also be used for monitoring and controlling industrial chemical or biotechnology production processes.

A method for measuring the viscosity of a fluid forms a second aspect of the present invention and comprises:
- providing a MEMS device having a preferably particle-protected measuring chamber comprising a micromechanical actuator, which is arranged in the manner of a cantilever above a metallically conductive ground plate and is elastically deformable towards the ground plate, and which is made of a metallically conductive, elastic material.
- surrounding the actuator with a fluid to be measured;
- connecting to the actuator a first output terminal of a two-terminal RF voltage source that can be switched off, and connecting to the counter electrode a second output terminal of the two-terminal RF voltage source that can be switched off;
- switching on the RF voltage source;
- detecting a change in the frequency, an amplitude or a phase of an RF signal measured at the RF voltage source or at a terminal of the actuator system comprising actuator and base plate
- determining a change in the frequency, amplitude or phase of the RF signal generated by the RF voltage source in order to determine therefrom a measurement value for the viscosity-dependent speed at which the actuator is deformed.

The method shares the advantages of the MEMS device according to the invention. It is particularly suitable for measuring the viscosity in extremely small fluid volumes. Exemplary embodiments of the method according to the invention arise from the exemplary embodiments described above for the MEMS device according to the invention.

BRIEF DESCRIPTION OF THE DRAWINGS

The invention is described below using further exemplary embodiments with reference to the drawings, in which.

DETAILED DESCRIPTION

Figure 1:
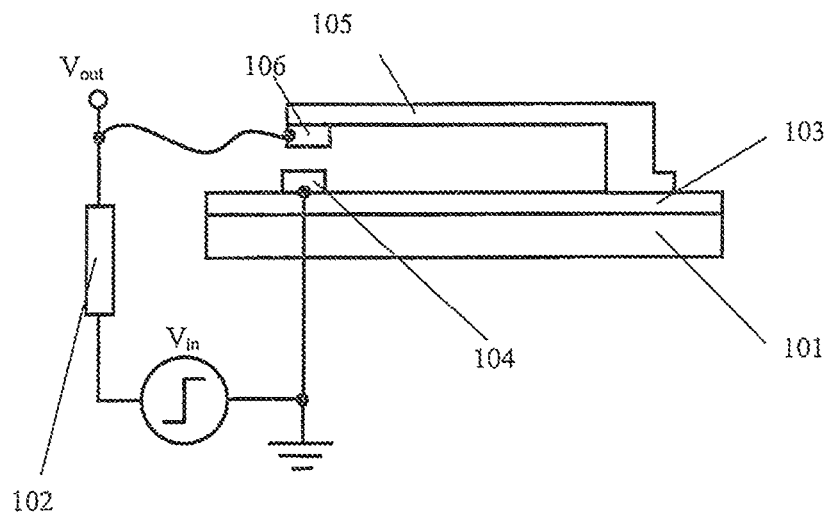
FIG. 1 shows an example of a micro-viscometer according to the prior art.
Figure 2:
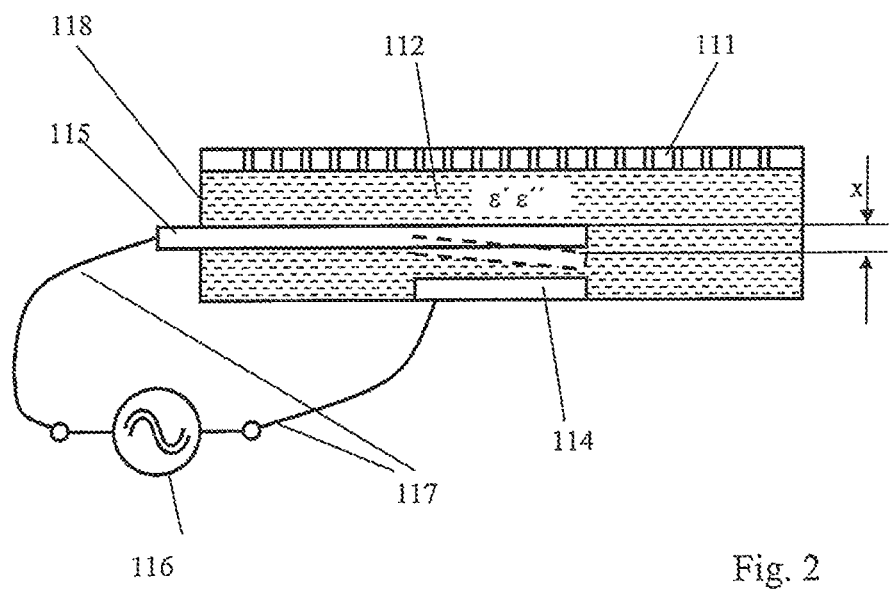
FIG. 2 shows in a plan view and side view an embodiment of an actuator in the form of a cantilever.

For the purpose of explaining an exemplary embodiment described below, FIG. 2 shows a schematic cross-sectional view of a measuring chamber 118 of a MEMS micro-viscometer. When an RF voltage is applied between an actuator in the form of an elastically deformable cantilever 115 and the counter electrode thereto, a ground electrode 114, a voltage is dropped between the electrode of the cantilever 115 and the ground electrode 114 across the fluid to be measured (measuring fluid) 111. As a result of the force of attraction between the electrodes, the cantilever 115 moves at a viscosity-dependent speed towards the counter electrode until the RF voltage is switched off by a measuring device which evaluates the frequency, an amplitude or a phase of the RF voltage.

The electrical properties of the fluid must not be ignored even when using an RF voltage to drive the actuator. The alternating current flowing through the fluid loads the RF voltage source according to the deflection of the actuator. In addition to the conductance, the permittivity, and hence the capacitance that is formed between the electrodes 114, 115, are determining factors.

The permittivity of a fluid to be measured is frequency dependent. It is composed of a real and imaginary part $$\in_r = \in_r' - j\in_r'' \quad (2)$$

Figure 3:
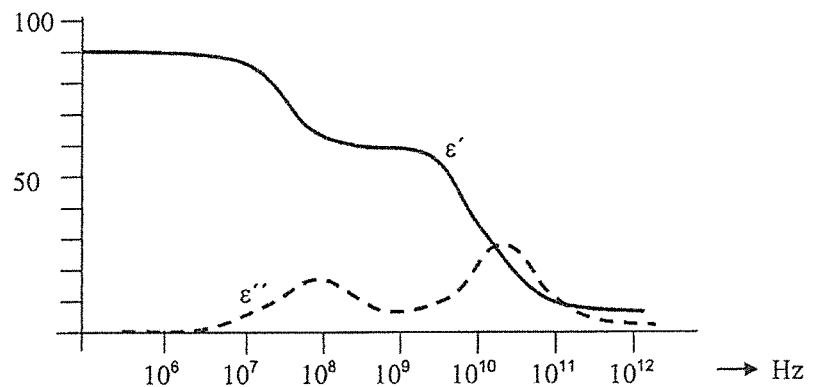
FIG. 3 shows a schematic diagram of the curve of the permittivity of a measuring fluid as a function of the frequency.

FIG. 3 shows as an example of a measuring fluid in the form of a measuring liquid a curve of the real part $\in_r'$ (continuous line) and the imaginary part $\in_r''$ (dashed line) of the permittivity $\in_r$ as a function of the frequency. It can be seen from the typical curves shown that for this fluid a frequency of the drive voltage of approximately 1 to 2 GHz is advantageous in order to minimize the effect of the iron movement on the measurement process. Moreover, in this frequency range both the real part and the imaginary part of the permittivity have only a low frequency dependency. In addition, the imaginary part is relatively small. This has the advantageous effect that heating of the measuring fluid as a result of dielectric losses is low. Heating of the measuring fluid would have an undesirable effect on the dielectric constants $\in_r'$ and $\in_r''$.

The total conductance, which is frequency dependent and related to the permittivity, can be found from the permittivity and the DC conductance:

$$\sigma_{AC}(\omega) = \sigma_0 + \sigma'(\omega) \quad (3),$$

where
- $\sigma_0$ denotes the DC conductance,
- $\omega$ the angular frequency,
- $\sigma'(\omega)$ the AC conductance, and
- $\sigma_{AC}(\omega)$ the frequency dependent total conductance.

Figure 4A:
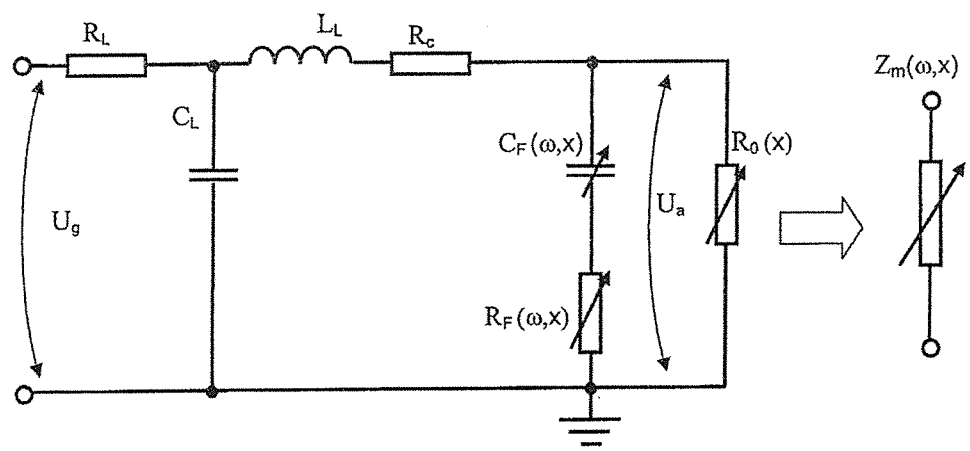
FIG. 4a shows an equivalent circuit of the actuator arrangement according to FIG. 5a (two-terminal device variant)

The electrical properties of measuring fluid, actuator, electrodes and supply lines can be summarized in the form of an equivalent circuit, which is shown in a simplified form in FIG. 4a. As an approximation, in this equivalent circuit, the properties of the measuring fluid are modelled as a parallel circuit of a resistor R0(x) and a lossy capacitor CF, RF, the values of which capacitor depend on the frequency and on the deformation of the actuator. It can also be seen from FIG. 4a that under realistic conditions the amplitude of a voltage Ua measurable between actuator and counter electrode (ground) is not equal to the amplitude of the RF alternating voltage ($U_G$) applied to the supply lines to the actuator and the counter electrode. This is caused by the electrical properties of the supply line, which are represented in a simplified form in FIG. 4a by a line resistance $R_L$, a line inductance $L_L$ and a line capacitance $C_L$. These elements shown in FIG. 4a are combined to produce a two-terminal device, the impedance of which depends on the frequency ω and a deformation measure x of the actuator 115.

Figure 4B:
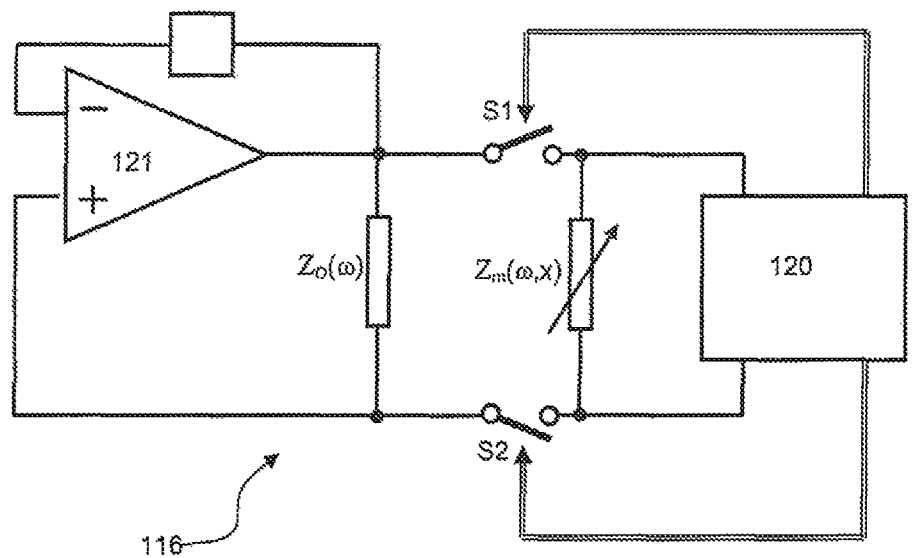
FIG. 4b, 4c show diagrams of an oscillator circuit that can be switched off having a two-terminal device and measuring instrument.

In one embodiment, as shown in a simplified form in FIG. 4b, this two-terminal device $Z_m(\omega,x)$ is inserted in an oscillator circuit as a frequency-determining component. This oscillator circuit is formed by an inverting feedback amplifier, at the output of which can already be a further frequency-determining component $Z_o(\omega)$. On switching the RF voltage lying at the output of the inverting amplifier 121 across the two-terminal device, in the MEMS device of this exemplary embodiment, not only is a drive voltage for the actuator generated but simultaneously the frequency of the RF oscillator is also measured in order to infer therefrom the deformation (e.g. deflection) of the actuator. The RF oscillator is therefore composed of the inverting amplifier 121 having its frequency-determining two-terminal device $Z_o(\omega)$ and the switched-across two-terminal device $Z_m(\omega,x)$. A movement of the actuator towards the metallically conducting counter electrode, which is grounded with respect to the RF voltage, changes the impedance between these electrodes and therefore also causes a change in the oscillator frequency. The movement continues until a defined frequency detuning Δf of the RF oscillator with respect to an initial frequency $f_0$, which occurs immediately after switching on, is reached, which is determined by the measuring device 120. This can be done e.g. using a frequency detector, phase-frequency detector or lock detector. A suitable reference frequency that is relatively constant over time is required at least for the two last variants, as explained below. If the frequency detuning Δf is reached, in the present example, the power supply of the RF oscillator or the connection of the RF oscillator to the actuator is disconnected. Here Ueff and Δf are selected so that the force of attraction acting on the actuator is sufficient to deflect same as far as mechanical contact with the counter electrode, while selecting Δf so that switching-off the power supply takes place at a distance between actuator and ground plate at which there is still no mechanical contact with the counter electrode. The time Δt that is required for the thus-defined deflection of the actuator is proportional to the viscosity and is recorded as a measure thereof. After switching off the power supply, the actuator returns to the initial position owing to its elastic restoring force, and the measurement process just described can be repeated cyclically at short time intervals by repeatedly switching on the power supply, and therefore a quasi continuous measurement of the viscosity is possible.

Figure 4C:
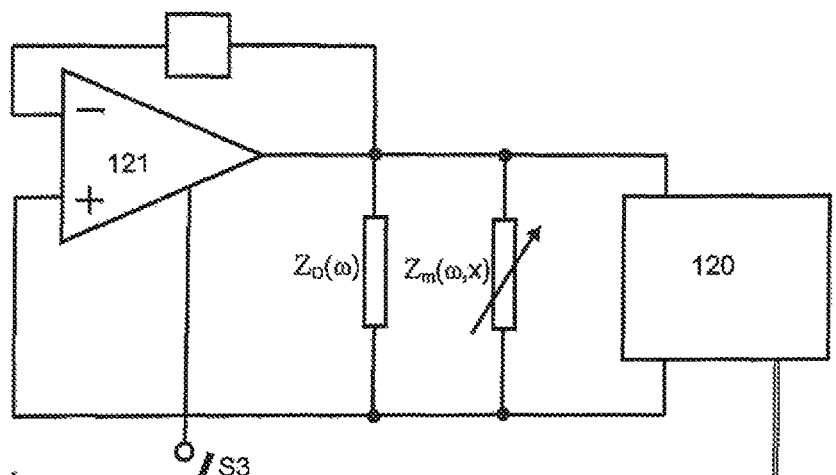

Switching-off the RF voltage is symbolized by way of example in FIG. 4b by a simple switching device, which can be used to close and open the connection between the RF oscillator and the two-terminal device $Z_m(\omega,x)$. Alternatively, however, switching on and off a supply of power to the measurement oscillator can be provided as shown in FIG. 4c.

Since the impedance of the two-terminal device Zm is not only determined by the deflection of the actuator but also by other parameters, some of which can vary during the measurement, a reference chamber which is assigned a second ring oscillator is provided in addition to the measuring chamber, as explained with reference to FIG. 5a.

Figure 5A:
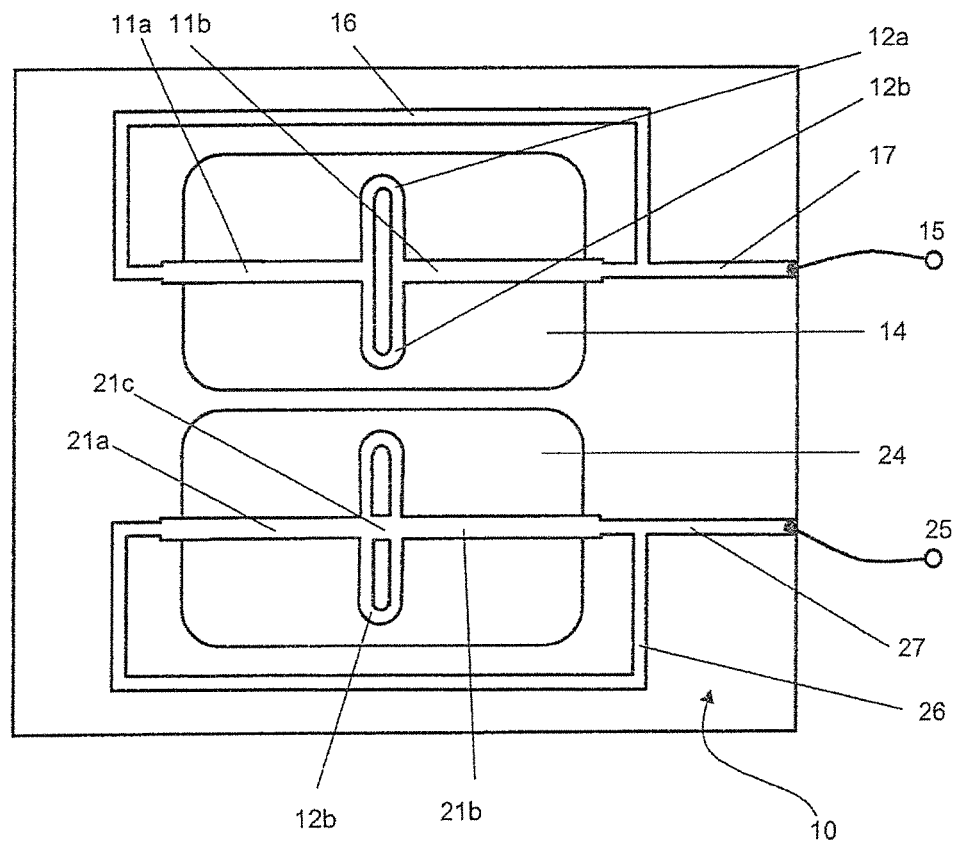
FIG. 5a shows a diagram of an actuator arrangement having a reference structure (two-terminal device variant)
Figure 5B:
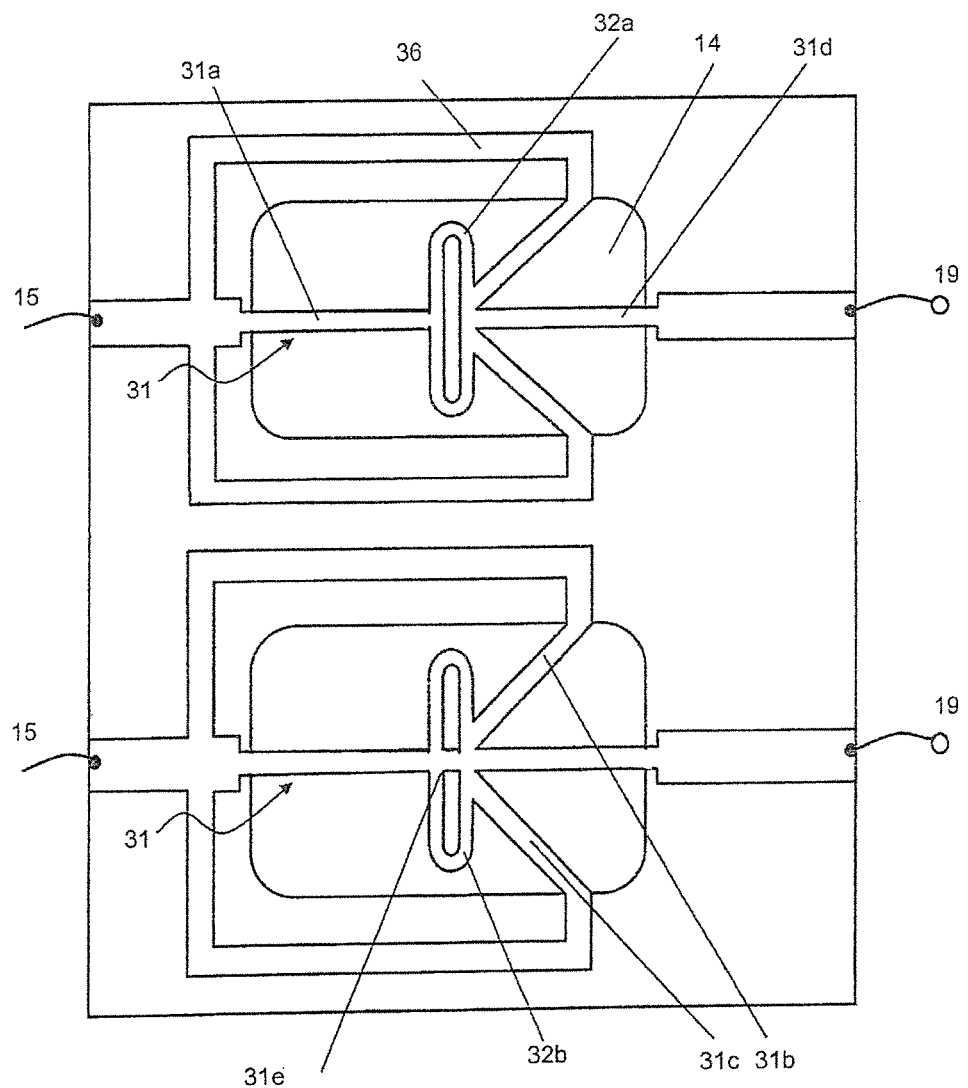
FIG. 5b shows a diagram of an actuator arrangement having a reference structure (two-port network variant)

FIG. 5a and FIG. 5b described below show diagrams of an actuator arrangement having a reference structure in a two-terminal device variant and in a two-pole network variant.

FIG. 5a shows a plan view of an arrangement of a measuring chamber 14 and a reference chamber 24 on a chip 10, as an exemplary embodiment of a MEMS device. Owing to the chosen perspective, the diagram in FIG. 5a does not show the MEMS device in full in the respect that, for example, it does not show counter electrodes in the measuring chamber 14 and the reference chamber 24 and connecting circuit elements. Both chambers 14 and 24 are also connected so as to allow fluid flow therebetween and hence contain the same measuring fluid during operation of the MEMS device.

Contact can be made to an actuator 11 in the measuring chamber 14 via a terminal 15 and track elements 16 and 17. The actuator 11 has two leaf springs 11a and 11b, which are connected by two elastic elements in the form of elastic U-pieces 12a and 12b. This arrangement forms together with a counter electrode (not shown here) and the measuring fluid a deformation-dependent capacitance. The actuator 11 is fixed at the two longitudinal ends thereof to an edge of the measuring chamber 14.

The reference chamber 24 contains a reference capacitance, which is structurally substantially identical to the capacitance in the measuring chamber 14. Contact can be made to a reference-actuator structure 21 in the reference chamber 14 via a terminal 25 and track elements 26 and 27. The reference-actuator structure likewise has two leaf springs 21a and 21b, which have the same shape and the same geometrical dimensions as the leaf springs 11a and 11b. The actuator 21 is also likewise fixed at the two longitudinal ends thereof to an edge of the reference chamber 24. In addition, the counter electrode in the reference chamber 24 is structurally identical to the counter electrode of the measuring chamber 14, although this is not apparent in the plan view of FIG. 5a. Unlike the situation for the actuator 11 in the measuring chamber 14, however, the U-pieces 22a and 22b are fixed by a rigid connecting link 21c. The reference actuator 21 therefore does not contain an elastic element. The reference actuator 21 is thereby substantially stiffer than the actuator 11. On applying an identical drive voltage to both actuators, the actuator 21 is deformed far less than the actuator 11, with the deformation equalling at most approximately 1% of the deformation of the actuator 11.

Figure 6:
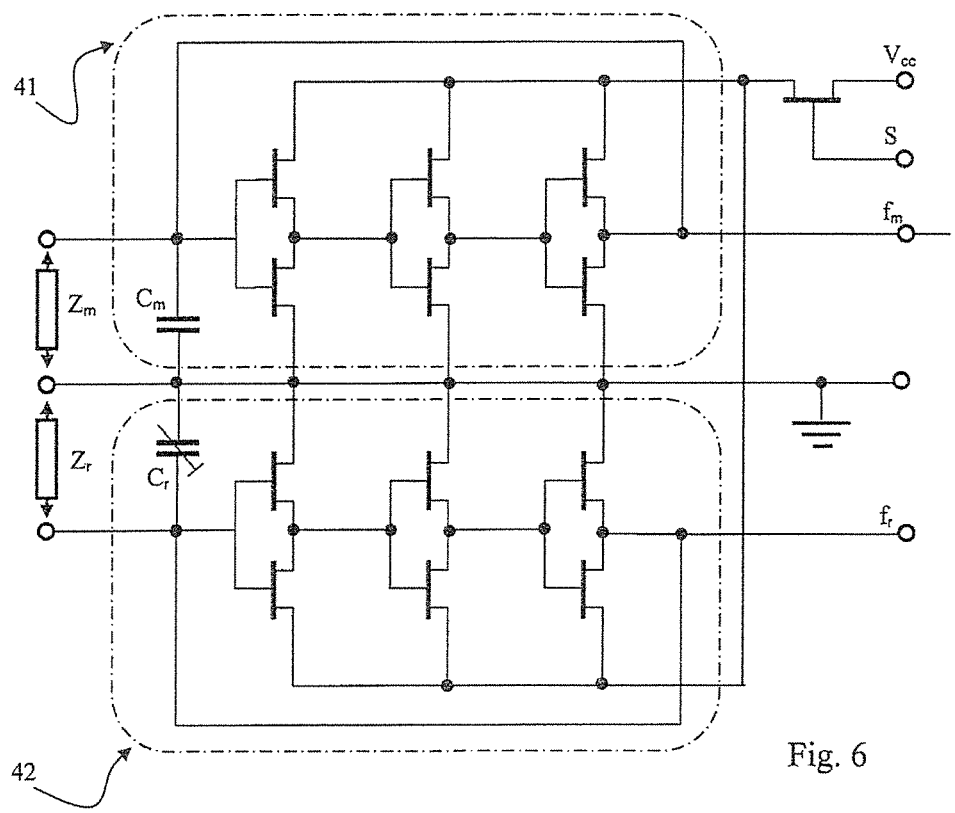
FIG. 6 shows a diagram of a two-terminal device variant having ring oscillator.

FIG. 6 shows as an exemplary embodiment a circuit diagram of the ring oscillators connected to the two measuring chambers described above. A CMOS ring oscillator 41 oscillating at approximately 3 GHz is used as the oscillator in this embodiment, as shown in the upper part of FIG. 6. The actuator is connected to a node between the output of one inverter stage of the ring oscillator and the input of the following stage of the ring oscillator. The impedance Zm of the two-terminal device in the measuring chamber affects the charge-transfer process of the base capacitance between two stages of the ring oscillator. An identically designed ring oscillator 42 shown in the bottom part of FIG. 6 is connected to the reference actuator structure 21 of FIG. 5a. A variable trimmer capacitor Cm, for example in the form of a MOS varactor, can be used to set the frequency of this reference ring oscillator so that it matches the frequency of the upper oscillator at the desired maximum deflection of the actuator. The initial frequency difference set in this way can be used to ensure that at the limit of travel of the actuator movement there is still no mechanical contact between counter electrode and actuator at the instant in time when the RF voltage source 116 switches off (instant when the frequencies are equal).

Figure 5C:
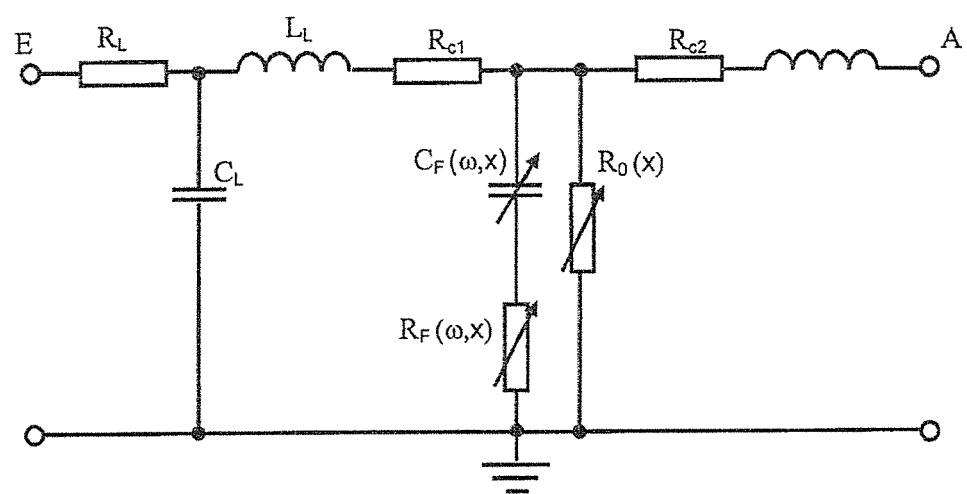
FIG. 5c shows an equivalent circuit of the actuator arrangement according to FIG. 5b (two-port network variant)
Figure 5C:
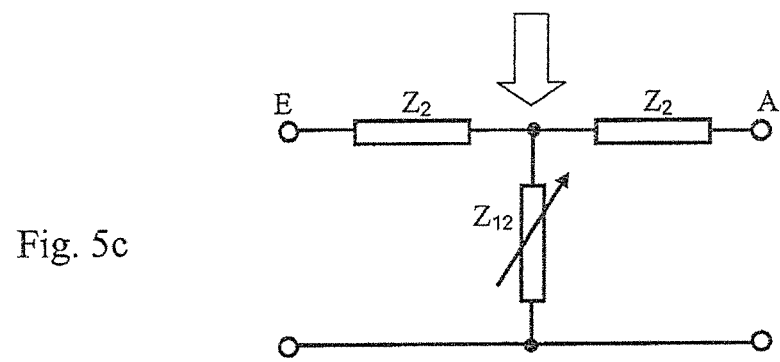
Figure 7:
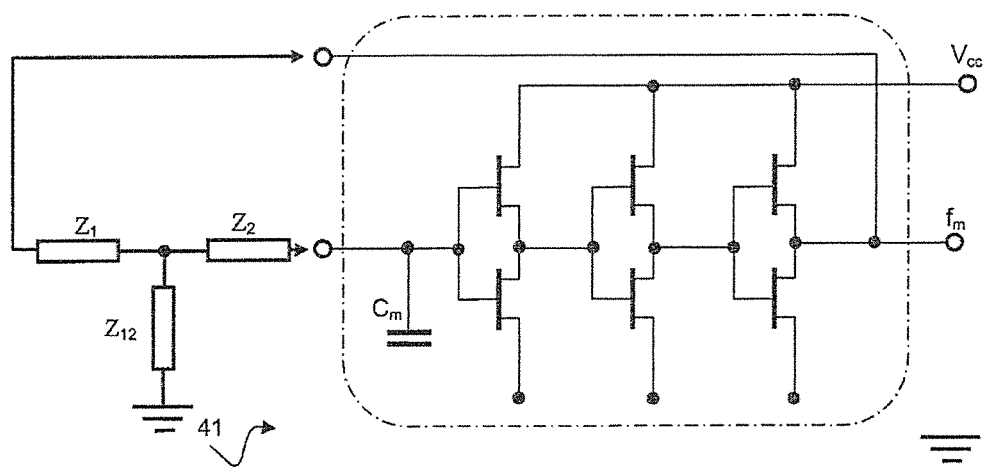
FIG. 7 shows a diagram of a two-port network variant having ring oscillator.

In a further embodiment of the invention, as shown in FIG. 5b, the actuator has a further electrical terminal from which an output signal 19 can be detected. The corresponding simplified electrical equivalent circuit can be represented as a two-port network, as illustrated in FIG. 5c. The resistors Rc1 and Rc2 here correspond to the intrinsic resistances of the actuator made of TiN. A deflection-dependent phase shift can be ascertained between the RF voltage at the terminals 15 and the RF voltage detected at the terminal 19 according to FIG. 6c or between the input E and the output A of the equivalent circuit in FIG. 5c. This two-port network is inserted between two inverter stages of the ring oscillator, as shown in FIG. 7.

Figure 8:
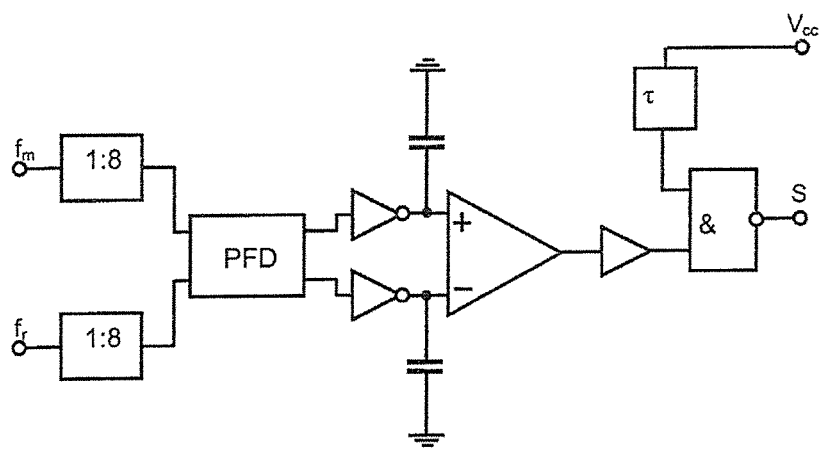
FIG. 8 shows a block diagram of a circuit arrangement having phase-frequency detector and switch-off device.

The frequency fm of the measurement oscillator 41, which contains the two-terminal device Zm as a frequency-determining component, can be measured at the ring oscillator 41 in the present exemplary embodiment. The same applies to the frequency fr of the reference oscillator 42. For this purpose, in this embodiment the measuring device 120 is connected to outputs provided for this reason of the two ring oscillators, and compares fm and fr during the measurement. FIG. 8 shows a possible implementation in circuitry of the frequency comparison in the measuring device 120. A phase-frequency detector PFD, the output of which is connected to a differential amplifier, provides when the frequencies are equal the signal for switching off the internal voltage supply. The thereby reduced power consumption is recorded by a monitoring circuit (not shown). This monitoring circuit is connected to a timer circuit, which records the time Δt between switching on (which is periodic in a preferred embodiment) the external power supply of the sensor chip and switching off the chip-internal power supply. A transceiver (not shown) can be used to communicate wirelessly the measurement values to an external analysis and display unit (not shown).

Figure 9:
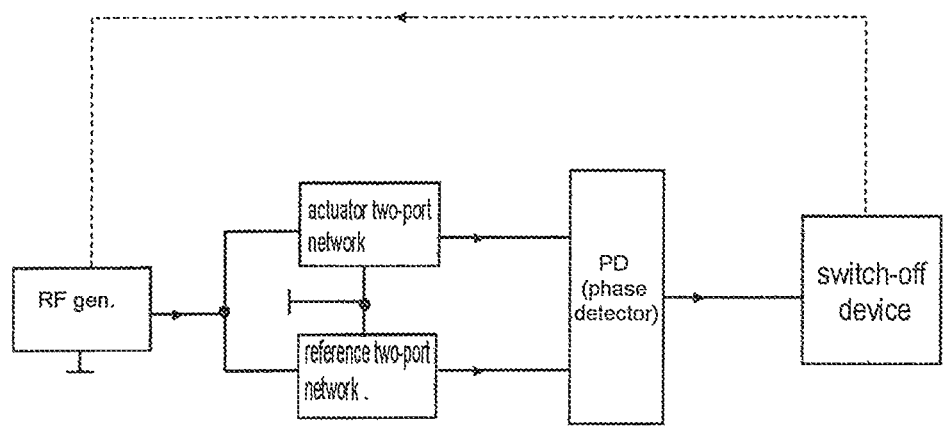
FIG. 9 shows a block diagram of a circuit arrangement having phase detector and switch-off device.

In another circuit variant using the actuator shown in FIG. 5b as a two-port network (FIG. 5c) in conjunction with a similarly designed reference structure without elastic element (lower part of FIG. 5b) it is also advantageously possible to use a phase detector (PD) instead of a PFD to monitor the U-piece movement. In this case, only one RF voltage source is required, which is connected both to the actuator and to the reference structure (FIG. 9). Here, during the actuator movement initiated by the RF voltage, the changed impedance of the two-port network does not alter the frequency of the RF voltage source but the phase of the voltage lying at the output 19 of the actuator structure (output A of the actuator two-port network. FIG. 5c). This phase is compared with the corresponding phase at the output of the reference structure that is not elastically flexible. Since in this measurement arrangement, the actuator is not part of a resonant circuit, the frequency of which is modified by the actuator impedance, the RF-generating oscillator can be decoupled from the output of the RF voltage source e.g. by a high-gain amplifier.

LIST OF REFERENCES 10 chip
11 actuator
11a, 11b leaf springs
12a, 12b elastic U-piece
14 measuring chamber
15 terminal
16, 17 track elements
19 two-port network output
21 reference actuator
21a, 21b leaf springs
21c connecting link
22a, 22b U-pieces
24 reference chamber
25 terminal
26, 27 track elements
31a-d leaf springs, actuator two-port network structure, reference two-port network structure
31e connecting link, two-port network structure
32a, 32b elastic elements (elastic U-piece), two-port network structure
36 track element, two-port network structure
41 RF voltage source/ring oscillator
42 reference voltage source/second ring oscillator
101 silicon substrate
102 series resistor
103 nitride layer
104 ground electrode
105 cantilever
106 counter electrode
110 capacitance measuring instrument
111 semipermeable membrane
112 measuring fluid
114 counter electrode
115 actuator
116 RF voltage source
117 connecting leads
118 measuring chamber
120 measuring device

The invention claimed is:

1. A micro-electromechanical device, referred to below as a MEMS device, for measuring the viscosity of a fluid, i.e. of a liquid or gas, which device comprises:
   a measuring chamber comprising a micromechanical actuator having a rest position, which is arranged in the manner of a cantilever above a metallically conductive counter electrode and is elastically deformable towards the counter electrode, and which during operation of the device must be surrounded by the fluid to be measured and is made of a metallically conductive material,
   a two-terminal RF voltage source that is switchable between on and off, a first output terminal connected to the actuator, and a second output terminal connected to the counter electrode, and which is designed to output an RF voltage signal having an RMS voltage that is suitable for deflecting the actuator out of its rest position, so that a laminar flow can develop temporarily in the fluid to be measured,
   a reference voltage source, which is designed to generate an RF reference signal that is substantially constant over time and is independent of the actuator movement, and
   a measuring device, which is designed to detect a change in a frequency, an amplitude or a phase of the RF voltage signal generated by the RF voltage source in order to determine therefrom a measurement value for a viscosity-dependent speed at which the actuator is deformed, wherein the measurement value for the viscosity-dependent speed is a timespan that is needed for a predefined deformation of the actuator in the fluid, wherein the deformation is defined so that no mechanical contact is made between the actuator and the counter electrode, wherein the measuring device is additionally designed to switch on the RF voltage source until the predefined deformation of the actuator is reached, at which time the RF voltage source is switched off, to determine the timespan between switching on and switching off the RF voltage source and to output a measurement signal that is dependent on the timespan as a measure of the viscosity of the fluid to be measured, and wherein the predefined deformation of the actuator is detected in the form of a predefined magnitude of a frequency difference, an amplitude difference or a phase difference that is reached between the RF reference signal output by the reference voltage source and the RF voltage signal.

2. The MEMS device according to claim 1, in which the RF voltage source is designed to output the RF voltage signal at a frequency at which, during operation of the MEMS device, a capacitive impedance between the actuator and the counter electrode, which impedance is dependent on the fluid to be measured, is less than an ohmic resistance that is dependent on a specific electrical conductivity of the fluid to be measured.

3. The MEMS device according to claim 1, in which the reference voltage source comprises a reference structure, which must be surrounded by the fluid to be measured during operation of the device, and in which dimensions of the reference structure and of the system formed by the actuator and counter electrode are identical or almost identical at least in the respect that the reference structure as a two-terminal device has an impedance that is identical or almost identical to the impedance that exists between the actuator and the counter electrode of the actuator system at the instant in time of switching off the RF voltage source.

4. The MEMS device according to claim 1, in which the measuring device switch on and switch off of the RF voltage source comprises either a frequency detector, a lock detector, a phase-frequency detector or a phase detector, each of which is designed to compare the frequency or phase of a RF voltage signal governed by the two-terminal RF voltage source with a RF voltage signal governed by the reference voltage source and, at the instant at which the frequency or phase of both RF signals is equal, to generate a switch-off signal.

5. The MEMS device according to claim 3, in which dimensions of the reference structure and of the system formed by the actuator and counter electrode are identical or almost identical at least in the respect that both are embodied as two-port networks, and an input impedance, output impedance and transimpedance are identical or almost identical for each at the instant in time of switching off.

6. The MEMS device according to claim 5, in which the reference structure comprises a reference chamber having a non-deformable reference actuator that has the same dimensions as the actuator, and in which the reference actuator must be surrounded by the fluid to be measured during operation of the device, is made of metallically conductive material and is arranged in the manner of a cantilever above a metallically conductive reference counter electrode.

7. The MEMS device according to claim 1, in which the RF voltage source is designed as a ring oscillator comprising an odd number of CMOS inverter stages, wherein an output from one of the CMOS inverter stages is connected to the actuator either directly or via a coupling capacitor, and an RF ground terminal of the ring oscillator is connected to the counter electrode.

8. The MEMS device according to claim 7, in which an actuator system embodied as a two-terminal device is connected directly or via a coupling capacitor to a connection between the output of one inverter stage of the ring oscillator and an input of an inverter stage following this inverter stage, and in which, because of a high resistance of the metallically conducting actuator material compared with a capacitive inductance $1/\omega C$, the frequency of the RF voltage source rises as a capacitive impedance $1/\omega C$ drops during movement of the actuator towards the counter electrode.

9. The MEMS device according to claim 7, in which an actuator system embodied as a two-port network having an input, an output and an RF ground, couples by a transimpedance of the two-port network two successive inverter stages of the ring oscillator in a form of a series circuit, wherein a first part of the actuator as an input of the two-port network is connected to an output of a first of two successive inverter stages, and a second part of the actuator as an output of the two-port network is connected to an input of a second of the two successive inverter stages.

10. The MEMS device according to claim 1, in which the measurement device is part of a measurement oscillator, and the reference voltage source is part of a reference oscillator, and in which both oscillators are designed to oscillate independently of one another, wherein the measurement oscillator supplies the RF voltage required for deforming the actuator, and wherein either the measurement oscillator or the reference oscillator additionally comprises a capacitance controlled by a control voltage.

11. The MEMS device according to claim 10, in which the voltage-controlled capacitance is dimensioned so that based on an initial frequency difference that is set by said capacitance, at the time of switching off the supply voltage at a limit of travel of the actuator movement, no mechanical contact is made between counter electrode and actuator.

12. The MEMS device according to claim 10, wherein said capacitance controlled by a control voltage is in the form of a varicap diode or a CMOS varactor, which is connected in parallel with a capacitance governing the frequency of the oscillator concerned.

13. The MEMS device according to claim 1, in which the actuator is fixed to an edge of the measuring chamber at at least two opposite points of the measuring chamber and comprises an elastic element.

14. The MEMS device according to claim 13, in which a reference actuator is fixed to an edge of a reference chamber at at least two opposite points of the reference chamber, but unlike the actuator, the reference actuator does not contain an elastic element.

15. The MEMS device according to claim 14, in which inputs of an actuator system embodied as a two-port network having an input, an output and an RF ground, and of a reference structure having the same embodiment as the actuator system, are connected to a common RF voltage source, and in which the measuring device comprises a phase detector (PD), which measures as the measurement signal for the actuator deformation, a phase difference between signals present at outputs of a two-port network of the actuator and of a two-port network of the reference actuator, which phase difference is modified by a deflection-induced impedance change of the two-port network of the actuator.

16. A method for measuring the viscosity of a fluid, comprising:
providing a MEMS device having a measuring chamber comprising a micromechanical actuator, which is arranged in the manner of a cantilever above a metallically conductive ground plate and is elastically deformable towards the ground plate, and which is made of a metallically conductive, elastic material;
surrounding the actuator with a fluid to be measured;
connecting to a terminal of the actuator a first output terminal of an RF voltage source that is switched off, and connecting to the ground plate a second output terminal of the RF voltage source that is switched off;
switching on the RF voltage source;
detecting a change in the frequency, an amplitude or a phase of an RF signal measured at the RF voltage source or at a terminal of an actuator system comprising the actuator and the ground plate; and
determining a change in the frequency, amplitude or phase of the RF signal generated by the RF voltage source in order to determine therefrom a measurement value for the viscosity-dependent speed at which the actuator is deformed,
wherein the measurement value for the viscosity-dependent speed is a timespan that is needed for a predefined deformation of the actuator in the fluid to be measured, wherein the deformation is defined so that no mechanical contact is made between the actuator and the counter electrode, wherein the measuring comprises switching on the RF voltage source, switching off the RF voltage source when the predefined deformation of the actuator is reached, determining the timespan between switching on and switching off the RF voltage source and outputting a measurement signal that is dependent on the timespan as a measure of the viscosity of the fluid to be measured, and wherein the predefined deformation of the actuator is detected in the form of a predefined magnitude of a frequency difference, an amplitude difference or a phase difference that is reached between an RF reference signal output by a reference voltage source and the RF voltage signal.

* * * * *